US00PP08689P

United States Patent [19]

Warriner, deceased

[11] Patent Number: Plant 8,689

[45] Date of Patent: Apr. 19, 1994

[54] CLIMBING ROSE PLANT NAMED 'JACARCH'

[75] Inventor: William A. Warriner, deceased, late of Tustin, Calif., by Alene B. Warriner, legal representative

[73] Assignee: Bear Creek Gardens, Inc., Medford, Oreg.

[21] Appl. No.: 18,761

[22] Filed: Feb. 17, 1993

[51] Int. Cl.[5] ..... A01H 5/00

[52] U.S. Cl. ..... Plt./3

[58] Field of Search ..... Plt. 1-3, Plt. 23

*Primary Examiner*—Howard J. Locker

*Attorney, Agent, or Firm*—Klarquist, Sparkman, Campbell, Leigh and Whinston

[57] ABSTRACT

A climber rose having a vigorous, arching, climbing habit of growth; healthy, dark green, glossy foliage; recurrent bloom; resistance to disease; and ability to survive in Zone 5 of the U.S.D.A. Cold Hardiness Map.

1 Drawing Sheet

The present invention relates to a new and distinct variety of rose plant of the climber class which was originated by the inventor by crossing the variety KORbin, with the variety Prairie Fire.

The primary objective of this breeding was to produce a new rose variety having the repeat flowering, healthy foliage, vigor and cold hardiness of the female parent combined with the cold hardiness, healthy foliage and arching climbing canes of the male parent. The objective was substantially achieved along with other desirable improvements as evidenced by the following unique combination of characteristics which are outstanding in the new variety and which distinguish it from its parents, as well as from all other varieties:

1. Heavy production of flowers produced throughout the growing season;
2. Long arching or climbing canes;
3. Glossy, dark green, disease-resistant foliage;
4. Excellent vigor; and
5. Cold hardiness in Zone 5 of the U.S.D.A. Cold Hardiness Map as established at Boerner Botanical Gardens, Milwaukee, Wis.

Asexual reproduction of this new variety by budding and hardwood cuttings, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—KORbin.

*Pollen parent.*—Prairie Fire.

Classification:

*Botanical.*—*Rosa hybrida.*

*Commercial.*—Climber.

FLOWERS

Observations made from specimens grown in a garden environment in Somis, Calif., from March through November, 1992.

Blooming habit: Recurrent.

Bud:

*Size.*—1¼ inches when the petals start to unfurl.

*Form.*—Long, pointed ovoid.

*Color.*—When sepals first divide, bud color is White Group 155B. When half blown, the upper and lower sides of the petals are White Group 155B.

*Sepals.*—Color: Green Group 138B. Surface texture: Covered in fine hairs. There are three lightly appendaged sepals. There are two unappendaged sepals with hairy edges.

*Receptacle.*—Color: Green Group 138A. Shape: Funnel. Size: Small. Surface: Smooth.

*Peduncle.*—Length: Short (1½-2 inches). Surface: Very glandular. Color: Light green and bronzy. Strength: Stiff, erect, slender.

Bloom:

*Size.*—Medium. Average open size is 2½-3 inches.

*Borne.*—Several together. If in clusters: Rounded.

*Stems.*—Long (Basal shoots to 5 to 6 feet with lateral stems terminating in flowers. Lateral stems 8-12 inches), strong.

*Form.*—When first open: High centered. Permanence: Flattens, outer petals curl back.

*Petalage.*—Number of petals under normal conditions: 25.

*Color.*—The upper and reverse sides of the petals are White Group 155B. The base of each petal has a small (¼×¼ inch), greenish yellow half moon at the point of attachment. The major color on the upper side is White Group 155B.

*Variegations.*—None.

*Discoloration.*—No change in the general tonality at the end of the first day or at the end of the third day.

*Fragrance.*—Moderate.

Petals:

*Texture.*—Thick.

*Shape.*—Round to slightly deltoid.

*Form.*—Tips slightly recurved.

*Arrangement.*—Imbricated, with no petaloids in the center.

*Persistence.*—Drop off cleanly.

*Lastingness.*—On the plant: Fair (3-5 days). As a cut flower: Fair (5 days).

Reproductive parts:

*Anthers.*—Size: Medium. Quantity: Many. Color: Yellow. Arrangement: Regular around styles.

*Filaments.*—Color: Yellow.

*Pollen.*—Color: Gold yellow.

*Styles.*—Color: Red.

*Stigmas.*—Color: Greenish white.

Form: Climber.

Growth: Very vigorous, arching or climbing.

Foliage:

*Number of leaflets on normal mid-stem leaves.*—5 or 7.

*Size.*—Medium (5×4 inches).

*Quantity.*—Abundant.

*Color.*—New foliage: Red. Old foliage: Dark green, glossy. Green Group 139A.

Leaflets:

*Shape.*—Pointed oval.

*Texture.*—Upper side: Leathery, glossy.

*Edge.*—Serrated.

*Serration.*—Single, small.

*Petiole rachis.*—Color: Green.

*Petiole underside.*—Smooth, with occasional prickles.

*Stipules.*—Medium, bearded.

*Disease resistance.*—Resistant to mildrew and rust under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Medium, hooked slightly downward.

*Color when young.*—Red.

Small Prickles:

*Quantity: On main stalks: None. On laterals: None.*

It is claimed:

1. A new and distinct variety of rose plant of the climber class, substantially as herein shown and described, characterized particularly as to novelty by the unique combination of its vigorous, arching, climbing habit of growth; healthy, dark green, glossy foliage; recurrent bloom; resistance to disease; and ability to survive in Zone 5 of the U.S.D.A. Cold Hardiness Map.

* * * * *

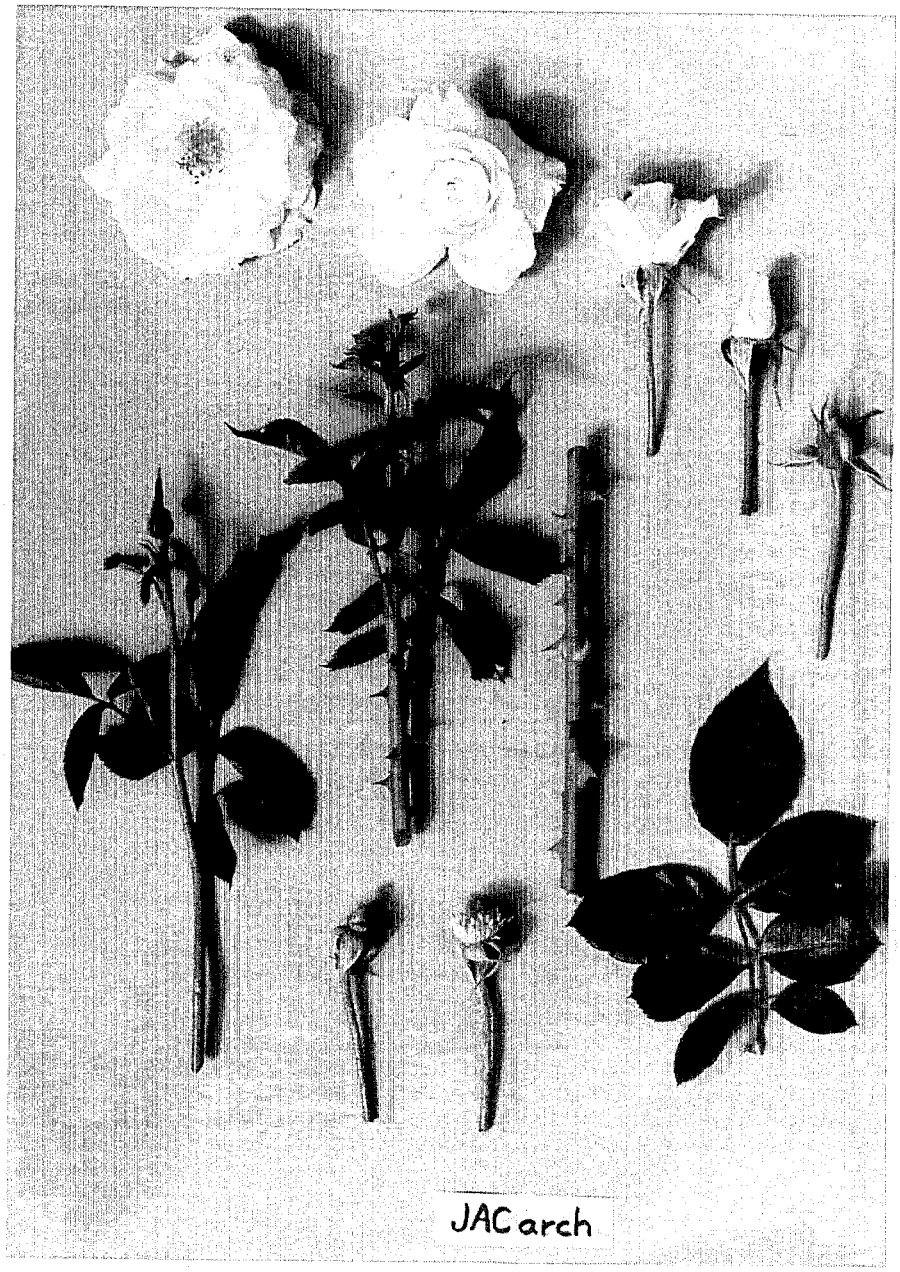
JACarch